United States Patent [19]

James et al.

[11] Patent Number: 5,786,301
[45] Date of Patent: Jul. 28, 1998

[54] N-BENZOTRIAZOLES

[75] Inventors: Donald R. James, El Sobrante; Raymond A. Felix, Richmond, both of Calif.

[73] Assignee: Zeneca Limited, London, England

[21] Appl. No.: 694,368

[22] Filed: Aug. 8, 1996

Related U.S. Application Data

[63] Continuation of Ser. No. 345,093, Nov. 28, 1994, abandoned, which is a continuation-in-part of Ser. No. 54,573, Apr. 28, 1993, Pat. No. 5,369,086.

[51] Int. Cl.$^6$ .......................... A01N 43/38; C07D 249/18
[52] U.S. Cl. .......................... 504/261; 548/259; 548/260; 548/261; 548/113; 548/257
[58] Field of Search .......................... 504/261; 548/257, 548/259, 260, 261, 113

[56] References Cited

U.S. PATENT DOCUMENTS

| | | | |
|---|---|---|---|
| 4,086,242 | 4/1978 | Diehl et al. | 514/340 |
| 4,240,822 | 12/1980 | Diehl et al. | 548/259 |
| 4,474,599 | 10/1984 | Rogers et al. | 544/336 |
| 4,950,678 | 8/1990 | Carney et al. | 514/340 |

FOREIGN PATENT DOCUMENTS

| | | |
|---|---|---|
| 0 107 216 | 5/1994 | European Pat. Off. |
| 536 847 | 6/1973 | Switzerland |

OTHER PUBLICATIONS

Hussein et al., CA 95: 4300h, 1981.
Elguero et al., CA 96: 142149 1982.
Siegrist CA 95:132759 1981.
Hussein et al., CA 93: 168201, 1980.
Balicka et al., CA 84:105497 1975.
Tsujimoto et al., CA 85:32162 1976.
Ejmocki, Z., Chemical Abstracts, vol. 86, No. 7, Feb. 14, 1977, Columbus, Ohio, U.S.; Abstract No. 42730u, "Use of the SNAr reaction for transformation of halonitrobenzene derivatives into biologically active agrochemicals", p. 457.
Chen, M., et al., Chemical Abstracts, vol. 114, No. 3, Jan. 21, 1991, Columbus, Ohio, US; Abstract No. 23894f, "Studies on fluorine containing heterocyclic compounds. 4. Reaction of 3–nitro–4–chlorobenzotrifluoride and 3,5–dinitro–4–chlorobenzotrifluoride with five–membered heterocycles", p. 701.
Dal Monte, D., et al., Chemical Abstracts, vol. 53, No. 17, Sep. 10, 1959, Columbus, Ohio, US; Abstract No. 16120d, "Triazoles and benzotriazoles".
Maquestiau, A., et al., Bulletin Des Societes Chimiques Belges, "Asynthese et reactions de deplacement nucleophile de derives nitres et halogenes due [3,2–b]pyrindo[4,5] benzo–1,3a,6,6a–tetraazapentalene", vol. 93, No. 11, 1984, Oxford GB, pp. 973–982.
Beilstein Registry No. 577633, Database Crossfire, Beilstein Informationssysteme GmbH, Frankfurt DE.
Beilstein Registry No. 577111, Database Crossfire, Beilstein Informationssysteme GmbH, Frankfurt DE.
Beilstein Registry No. 562762, Database Crossfire, Beilstein Informationssysteme GmbH, Frankfurt DE.
Beilstein Registry No. 562764, Database Crossfire, Beilstein Informationssysteme GmbH, Frankfurt DE.
Beilstein Registry No. 562763, Database Crossfire, Beilstein Informationssysteme GmbH, Frankfurt DE.
Beilstein Registry No. 4213271, Database Crossfire, Beilstein Informationssysteme GmbH, Frankfurt DE.
Beilstein Registry No. 4204771, Database Crossfire, Beilstein Informationssysteme GmbH, Frankfurt DE.
Beilstein Resgistry No. 168115, Database Crossfire, Beilstein Informationssysteme GmbH, Frankfurt DE.
Beilstein Registry No. 168177, Database Crossfire, Beilstein Informationssysteme GmbH, Frankfurt DE.
Beilstein Registry No. 220853, Database Crossfire, Beilstein Informationssysteme GmbH, Frankfurt DE.
Beilstein Registry No. 276844, Database Crossfire, Beilstein Informationsysteme GmbH, Frankfurt DE.
Beilstein Registry No. 5613120, Database Crossfire, Beilstein Informationssysteme GmbH, Frankfurt DE.
Beilstein Registry No. 522335, Databse Crossfire, Beilstein Informationssysteme GmbH, Frankfurt DE.
Beilstein Registry No. 6514276, Database Crossfire, Beilstein Informationssysteme GmbH, Frankfurt DE.
Beilstein Registry No. 277018, Database Crossfire, Beilstein Informationssysteme GmbH, Frankfurt DE.
Beilstein Registry No. 270981, Database Crossfire, Beilstein Informationssysteme GmbH, Frankfurt DE.
Beilstein Registry No. 235222, Database Crossfire, Beilstein Informationssysteme GmbH, Frankfurt DE.
Beilstein Registry No. 233391, Database Crossfire, Beilstein Informationssysteme GmbH, Frankfurt DE.
Beilstein Registry No. 222126, Database Crossfire, Beilstein Informationssysteme GmbH, Frankfurt DE.

(List continued on next page.)

*Primary Examiner*—Jane Fan
*Attorney, Agent, or Firm*—Melissa A. Shaw

[57] ABSTRACT

This invention relates to substituted N-benzotriazoles of the formula

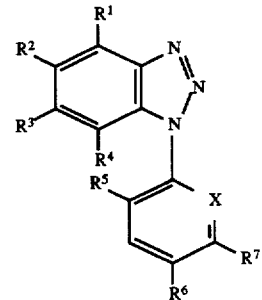

in which:

$R^1$, $R^2$, $R^3$, $R^4$, $R^5$, $R^6$, $R^7$, X are as defined in the specification. The compounds exhibit herbicidal activity.

15 Claims, No Drawings

OTHER PUBLICATIONS

Beilstein Registry No. 256542, Database Crossfire, Beilstein Informationssysteme GmbH, Frankfurt DE.

Beilstein Registry No. 270982, Database Crossfire, Beilstein Informationssysteme GmbH, Frankfurt DE.

Beilstein Registry No. 222117, Database Crossfire, Beilstein Informationsysteme GmbH, Frankfurt DE.

Beilstein Registry No. 220780, Database Crossfire, Beilstein Informationsysteme GmbH, Frankfurt DE.

Beilstein Registry No. 220764, Database Crossfire, Beilstein Informationsysteme GmbH, Frankfurt DE.

Beilstein Registry No. 220779, Database Crossfire, Beilstein Informationssysteme GmbH, Frankfurt DE.

Beilstein Registry No. 804619, Database Crossfire, Beilstein Informationssysteme GmbH, Frankfurt DE.

Beilstein Registry No. 219608, Database Crossfire, Beilstein Informationssysteme GmbH, Frankfurt DE.

Beilstein Registry No. 617768, Database Crossfire, Beilstein Informationssysteme GmbH, Frankfurt DE.

Beilstein Registry No. 613954, Database Crossfire, Beilstein Informationssysteme GmbH, Frankfurt DE.

Beilstein Registry No. 617770, Database Crossfire, Beilstein Informationssysteme GmbH, Frankfurt DE.

Beilstein Registry No. 529329, Database Crossfire, Beilstein Informationssysteme GmbH, Frankfurt DE.

Beilstein Registry No. 6508248, Database Crossfire, Beilstein Informationssysteme GmbH, Frankfurt DE.

Pr. Nauk., Politech. Warsz., Chem., 17 (1975), p. 51.

N-BENZOTRIAZOLES

This application is a continuation of application Ser. No. 08/345,093, filed Nov. 28, 1994, now abandoned which was a continuation-in-part of application Ser. No. 08/054,573, filed Apr. 28, 1993, now U.S. Pat. No. 5,369,086.

BACKGROUND AND SUMMARY OF THE INVENTION

This invention relates to substituted N-benzotriazoles of the formula

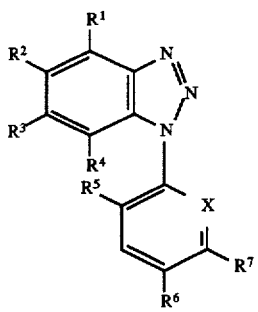

in which:

$R^1$, $R^2$ and $R^3$ may independently be hydrogen; halogen; nitro; hydroxy; cyano; alkyl; amino; alkoxyiminoalkyl; cyanoalkyl; carboxyalkyl; carboalkoxyalkyl; cyano (carboalkoxy)alkyl; hydroxyalkyl; alkoxyalkyl; alkylsulfonylamino-alkyl; haloalkylsulfonylaminoalkyl; (alkyl)$_n$aminoalkyl; (alkylcarbonyloxy)$_2$alkyl; haloalkyl; formyl; alkylcarbonyl; carboxy or its salts; COOalkyl; carboxamido; mono or di-substituted carboxamido wherein the nitrogen substituents can be selected from hydrogen, alkyl, haloalkylsulfonyl, and alkylsulfonyl; sulfonamido wherein the nitrogen substituents can be selected from hydrogen and alkyl; (alkylsulfonyl)$_2$amino; (acetyl)$_2$amino;

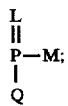

and $YR^8$ wherein Y is O, $NR^9$, or $S(O)_n$; and $R^8$ is —($R^{10}$)$_m$—$COR^{11}$; —($R^{10}$)$_m$—$SO_2R^{11}$;

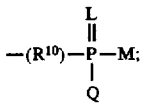

alkyl; haloalkyl; hydroxyalkyl; aralkyl; cyanoalkyl; acetoxyalkyl; alkoxyalkyl; hydroxy; alkenyl or alkynyl;

$R^9$ is hydrogen; alkyl; alkynyl, alkenyl or alkylcarbonyl;
$R^{10}$ is alkylene;
$R^{11}$ is alkyl; haloalkyl; hydrogen, hydroxy; alkoxy; haloalkoxy; alkoxyalkyl; alkoxyalkoxy; alkoxyalkylamino; dialkoxyalkylamino; aryloxy; aralkyl; alkoxycarbonyl; hydroxy-carbonyl; alkoxycarbonylalkyl; hydroxycarbonylalkyl; (alkyl)$_n$-amino; (alkyl)$_n$hydrazino; alkoxycarbonylalkylamino; hydroxy-alkylamino; (alkyl)$_n$aminoalkylamino; (alkyl)$_n$aminocarbonyl-alkylamino; hydroxycarbonylalkylamino; alkylsulfonylamino; arylsulfonylamino; acetylaminoalkylamino; N-alkoxy-N-(alkyl)$_m$amino; N-hydroxy-N-(alkyl)$_m$amino; cyanoalkylamino; (alkenyl)$_n$-amino; alkoxyalkylamino; (alkynyl)$_n$amino; alkenyloxy; alkynyloxy or semicarbazido;

or $R^2$ and $R^3$ taken together with the carbon atom to which they are attached comprise an optionally substituted saturated or unsaturated heterocyclic ring having up to 6 ring members selected from carbon, nitrogen, oxygen and sulfur and wherein the substituents are selected from alkyl, alkoxy, halogen, haloalkyl, cyano, carboxy, formyl, oxo and carboalkoxy;

or $R^3$ is —(CH$_2$)$_q$ $R^{14}$ where $R^{14}$ is a 5, 6 or 7 membered saturated or unsaturated optionally substituted heterocyclic ring wherein the ring members are selected from the group consisting of nitrogen, carbon, oxygen and sulphur and wherein the substituents are selected from the group consisting of alkyl, alkoxy, halogen, haloalkyl, cyano, carboxy, formyl, oxo and carboalkoxy;

or $R^3$ is $YR^8$ where $R^8$ or $R^{11}$ can be a 5, 6 or 7 membered saturated or unsaturated optionally substituted heterocyclic ring wherein the ring members are selected from nitrogen, carbon, oxygen and sulphur and the substituents are selected from alkyl, alkoxy, halogen, haloalkyl, cyano, carboxy, formyl, oxo and carboalkoxy;

m is 0 or 1;
n is 0, 1 or 2;
z is 1 or 2;
q is 0 or 1;

M and Q are independently alkoxy; alkyl; (alkyl)$_n$-amino; hydroxy; hydrogen; alkenyloxy; (alkenyl)$_n$amino; alkynyloxy; or (alkynyl)$_n$amino;

L is oxygen or sulfur;
P is phosphorus;
$R^4$ is hydrogen, halogen, alkyl or nitro;
$R^5$ is hydrogen; nitro; halogen; cyano; alkylthio; alkylsulfinyl; alkylsulfonyl; alkoxy; acetylamino or amino;
$R^6$ is hydrogen; halogen; haloalkyl; haloalkoxy; cyano or $SO_yR^{12}$ and $R^{12}$ is alkyl or haloalkyl and y is 0, 1 or 2;
$R^7$ is hydrogen or halogen;
X is N or $CR^{13}$ wherein $R^{13}$ is hydrogen; halogen; haloalkyl; cyano; nitro; alkylthio; alkylsulfonyl; alkylsulfinyl or alkoxy; and agriculturally acceptable salts thereof.

DESCRIPTION OF THE INVENTION

Within the scope of the above formula certain embodiments are preferred as follows:

$R^1$ is hydrogen; halogen; cyano; alkyl and haloalkyl. More preferably hydrogen, halo and cyano.

$R^2$ is hydrogen; nitro; alkyl; halogen; alkoxy; carbonylalkoxy; haloalkyl; haloalkoxy; COOalkyl; SO$_3$H and $YR^8$ wherein Y is O, $NR^9$ and $S(O)_n$.

$R^3$ is hydrogen; alkyl; halogen; hydroxy; haloalkyl; amino; a 5, 6 or 7 member heterocyclic ring wherein the heterocyclic ring is attached to the benzotriazole ring by a N-atom or $YR^8$ wherein Y is O, $NR^9$ or $S(O)_n$ and $R^8$ is (—$R^{10}$)$_m$COR$^{11}$, cyanoalkyl, alkenyl, alkynyl, haloalkyl, alkoxy-alkyl and alkyl; $R^9$ is hydrogen, alkyl and alkylcarbonyl and $R^{11}$ is alkoxy, alkyl and alkynyloxy.

$R^4$ is hydrogen and alkyl.
$R^5$ is hydrogen and halogen.
$R^6$ is an $SO_yR^{1212}$. More preferably haloalkyl.
$R^7$ is hydrogen.
$R^{10}$ is —CH$_2$—, —CH$_2$CH$_2$— or —CH(CH$_3$)—.
X is N or $CR^{13}$ wherein $R^{13}$ is hydrogen, halogen or haloalkyl. More preferably N or C-chloro.

A preferred embodiment comprises $R^1$ is hydrogen, alkyl, cyano, halogen, haloalkyl or alkoxy; $R^2$ is hydrogen, halogen, alkyl, nitro, alkoxy, haloalkyl, COOalkyl, or OR$^8$; $R^3$ is hydrogen, alkyl, halogen, hydroxy or $YR^8$; $R^4$ is hydrogen; $R^5$ is halogen or hydrogen; $R^6$ is haloalkyl or $SO_xR^{12}$; $R^7$ is hydrogen and X is N or C-chloro.

Another preferred embodiment comprises $R^1$ hydrogen, alkyl or halogen; $R^2$ is hydrogen or halogen; $R^3$ is a 5, 6 or 7 membered saturated or unsaturated optionally substituted heterocyclic ring wherein the ring members are selected from the group consisting of nitrogen, carbon, oxygen and sulphur and wherein the heterocyclic ring is attached to the benzo-triazole by a N-atom; $R^4$ is hydrogen; $R^5$ is hydrogen or halogen, $R^6$ is haloalkyl; $R^7$ is hydrogen and X is N or C-halogen.

Another preferred embodiment comprises $R^1$ is hydrogen, halogen, alkyl or haloalkyl; $R^2$ is hydrogen, alkyl or halogen; $R^3$ is $YR^8$; $R^4$ is hydrogen, $R^5$ is hydrogen or halogen; $R^6$ is haloalkyl; $R^7$ is hydrogen; X is N, C-halogen or C-hydrogen.

A further preferred embodiment comprises $R^1$ is hydrogen; $R^2$ is chloro or fluoro; $R^3$ is $YR^8$ wherein Y is O, $NR^9$, or $S(O)_n$; $R^4$ is hydrogen; $R^5$ is chloro; $R^6$ is haloalkyl; $R^7$ is hydrogen and X is N.

The above described embodiments are illustrative of the invention and are not intended to limit the invention whatsoever.

The term "alkyl" and all groups containing alkyl portions are intended to include straight-chain, branched-chain and cyclic groups. Examples are methyl, ethyl, n-propyl, isopropyl, cyclopropyl, n-butyl and t-butyl. Each alkyl member may contain one to six carbon atoms. For example, $(C_1-C_6)$alkoxy$(C_1-C_6)$alkoxy; amino $(C_1-C_6)$ alkylcarbonyl. Similarly the terms alkenyl and alkynyl refer to unsaturated or branch chains having from two to six carbon atoms.

In the above definitions, the term "halogen" includes fluoro, chloro, bromo and iodo groups. The term "haloalkyl" refers to the alkyl group substituted by one or more halogen atoms.

Heterocyclic ring shall mean saturated or unsaturated rings containing at least one atom of nitrogen, oxygen or sulphur. Examples include azole, furan, imidazole, isopyrrole, morpholine, oxazole, piperazine, piperidine, pyridine, pyrimidine, thiazole, thiophene and triazole.

Also included in the invention are the stereo and optical isomers of the compounds claimed and mixtures of these isomers in all proportions.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing and the like. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally-acceptable salts" is used herein to denote a salt or salts which readily ionize in aqueous media and includes sodium, potassium, calcium, ammonium, magnesium salts and acid salts such as hydrochloride, sulfate and nitrate.

The compounds of the present invention have been found to be active herbicides, possessing utility as pre-emergence and post-emergence herbicides and useful against a wide range of plant species including broadleaf and grassy species. Some of the compounds demonstrate selective control of plant species in certain crops, such as rice, corn and soybean.

This invention therefore also relates to a method for controlling undesirable vegetation comprising applying to a locus where control of such vegetation is desired, either prior or subsequent to the emergence of such vegetation, an herbicidally effective amount of a compound as described herein, together with an inert diluent or carrier suitable for use with herbicides.

The N-benzotriazole compounds of the invention may be prepared by the following exemplary general procedure described herein below.

GENERAL DESCRIPTION

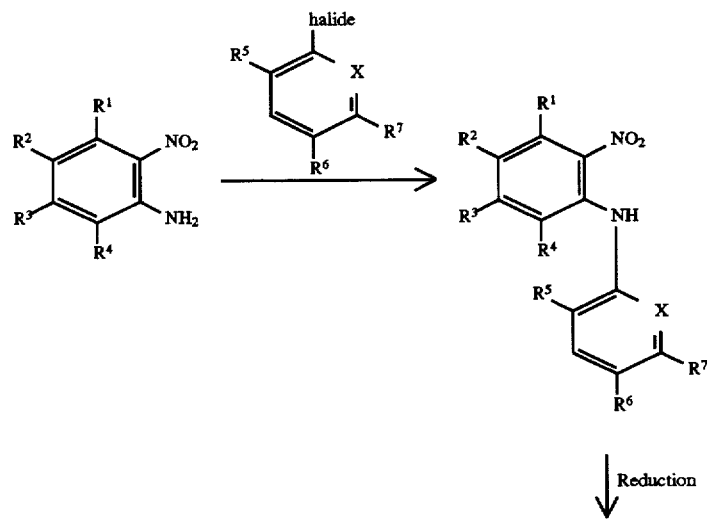

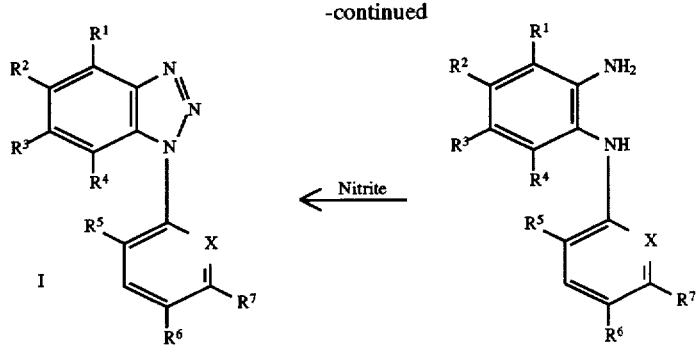

Here, the ortho-Nitro anilines, prepared by nitration, of the corresponding anilide are readily arylated with the appropriate aryl halide in the presence of a base such as sodium hydride or potassium carbonate in an inert solvent such as N,N-dimethylformamide (DMF) or dimethyl sulfoxide at temperatures between 0° C. and 100° C. The halide leaving group can be fluoro, chloro or bromo. The ortho-Nitro intermediates are then readily reduced with iron in an alcohol/water mixture or by stannous chloride or other reducing metals salts in a similar manner. The resulting 1,2-phenylenediamines are readily cyclized to the final products with a source of nitrite, either inorganic metal nitrite salts in the presence of acid or organic nitrites such as isoamyl nitrite with-or-without an acid catalyst.

The final products produced by the above-described process can be further reacted to introduce particular substitutents on the benzotriazole moiety, especially at the 6-position. For example, a compound of formula (I) wherein $R^3$ is hydroxy can be reacted with a substituted alkyl halide or sulfonate to produce a compound of formula (I) wherein $R^3$ is a substituted alkyl group. To produce a compound of formula (I) wherein $R^3$ is a sulfonamide, a compound of formula (I) wherein $R^3$ is amino is reacted with a substituted sulfonic anhydride.

These examples are presented for purposes of illustration and are not intended as a restriction on the scope of the invention.

EXAMPLE 1

Preparation of 6-hydroxy-1-[2'-(3'-chloro-5'-trifluoromethyl)pyridyl]1[H]-benzotriazole (Compound 15 herein)

(a) M-anisidine (24.6 g, 200 mmol), acetic acid (200 ml) and acetic anydride (22.5 g, 220 mmol) were combined and stirred at ambient temperature for 30 minutes. The mixture was cooled and 50 ml (0.8M) concentrated nitric acid was added. The mixture was diluted with water to produce 35 g of 2-nitro-5-methoxy acetanilide.

(b) The product of step (a) was combined with 50 ml water, 100 ml concentrated hydrochloric acid and heated to reflux. The mixture was poured into water to yield 5.5 g 2-nitro-5-methoxy aniline.

(c) The product of step (b) (5.5 g, 33 mmol) was combined under nitrogen with 2, 3-dichloro-5-trifluoromethyl (7.1 g, 33 mmol) and 75 ml N,N-dimethylformamide (DMF). Sodium hydride (1.7 g, 71 mmol) was slowly added and the mixture was allowed to stir for 2.0 hours at ambient temperature. The mixture was poured slowly into dilute hydrochloric acid over ice to give 10.0 g of solid 2-nitro-5-methoxy-N-[2'-(3'-chloro-5'-trifluoromethyl)pyridyl] aniline.

(d) A mixture of 31.6 ml ethanol, iron (4.4 g, 70 mmol) reduced electrolytically, 26.3 ml water and 0.34 ml concentrated hydrochloric acid were heated to reflux. The product of step (c) (9.1 g, 26.3 mmol) was added to the above mixture while reflux was maintained. The resulting mixture was allowed to reflux for another 30 minutes, then cooled to 60°–65° C., neutralized with 50% sodium hydroxide (0.34 g), filtered through diatomaceous earth, stripped under vacuum, slurried with water and filtered to yield 7.7 g of 4-methoxy-2-[2'-(3'-chloro-5'-trifluoromethyl)pyridyl] 1,2-phenylene-diamine.

(e) The product of step (d) (3.18 g, 10 mmol) was combined with 30 ml dichloromethane and cooled to −70° C. Then there was added dropwise boron tribromide (3.8 ml, 40 mmol) dissolved in 6 ml dichloromethane. The reaction mixture was allowed to warm to ambient temperature then further cooled to −30° C. with the addition of 60 ml methanol. The mixture was stripped under vacuum. The residue was treated with aqueous sodium bicarbonate and extracted with dichloromethane, dried over magnesium sulfate ($MgSO_4$) and stripped under vacuum. The residue from the dichloromethane solubles was extracted with 200 ml methanol, stripped under vacuum and slurried in water to which sodium bicarbonate was added until the aqueous solubles became neutral to yield 3.0 g, 4-hydroxy-2-[2'-(3'-chloro-5'-trifluoromethyl)pyridyl] 1,2-phenylenediamine.

(f) The product of step (e) (2.0 g, 6.59 mmol) was combined with 20 ml, DMF, isoamyl nitrite (0.97 ml, 7.26 mmol), a few drops of methanesulfonic acid and stirred at ambient temperature overnight. To bring the reaction to completion an additional 0.1 ml isoamyl nitrite and a drop of methanesulfonic was added. The mixture was stripped under vacuum to yield a solid. The solid was further washed with water, filtered and dried to yield the claimed compound 6-hydroxy-1-[2'-(3'-chloro-5'-trifluoromethyl)pyridyl]1[H]-benzotriazole.

EXAMPLE 2

Preparation of 6-(cyano)methoxy-1-[2'-(3'-chloro-5'-trifluoromethyl)pyridyl]1[H]-benzotriazole (Compound 16 herein)

(a) 4-methoxy-2-[2'(3'-chloro-5'-trifluoromethyl)-pyridyl]-1,2-phenylene diamine (8.7 g, 27.4 mmol) was combined with 82 ml dichloromethane, cooled to −70° C. in a dry ice isopropanol bath and 10.4 ml (110 mmol) boron tribromide in 20 ml dichloromethane was added dropwise. The mixture was warmed to ambient temperature, and further cooled to −30° C. and 160 ml methanol added dropwise. The mixture was stripped under vacuum, neutralized with sodium bicarbonate, extracted with dichloromethane and filtered. The solids were extracted with methanol and stripped to yield 4.0 g of 4-hydroxy-2-[2'-(3'-chloro-5'-trifluoromethyl)pyridyl]-1,2-phenylenediamine.

(b) The product of step (a) (4.0 g, 13.2 mmol), was combined with 40 ml DMF, 1.95 g (14.5 mmol) isoamyl nitrite and 3 drops methanesulfonic acid (catalyst) and stirred overnight at ambient temperature. The mixture was stripped under vacuum, then extracted with dichloromethane and treated with water. The organic phase was dried over magnesium sulfate and stripped under vacuum to yield 3.1 g 6-hydroxy-2-[2'-(3'-chloro-5'-trifluoromethyl)pyridyl-1-H benzotriazole.

(c) The product of step (b) (1.9 g., 6 mmol) was combined with, 20 ml acetonitrile, 0.83 g (6 mmol) powdered potassium carbonate and bromoacetonitrile (0.46 ml, 6.6 mmol), heated at reflux for 1 hour and stripped under vacuum. The resulting solids were extracted in dichloromethane, treated with water, dried over magnesium sulfate, filtered and the dichloromethane solution stripped under vacuum.

The solids were then purified by extraction with hot hexanes/25% benzene and the solid product filtered to yield 0.9 g of the claimed compound, 6-(cyano)methoxy-1-[2'-(3'-chloro-5'-trifluoromethyl)pyridyl]1[H]-benzotriazole. The hexanes/benzene solution was stripped under vacuum, extracted with ether and the ether stripped under vacuum to yield another 0.4 g product after trituration.

EXAMPLE 3

Preparation of 5-methyl-6-methoxy-1-[2'-(3'-chloro-5'-trifluoromethyl)pyridyl]1[H]-benzotriazole (Compound 21 herein)

(a) 4-methyl-3-methoxy aniline, (7.6 g, 50 mmol) 6 ml acetic acid and 6 ml acetic anhydride were combined which produced an exotherm. The mixture was cooled to ambient temperature. Concentrated nitric acid (15 ml) which had been cooled in an ice bath was added. The mixture crystallized and was treated liberally with water to yield 7.8 g of 2-nitro-4-methyl-5-methoxy acetanilide solids.

(b) The product of step (a) (7.8 g, 34.7 mmol) was combined with 100 ml concentrated hydrochloric acid and heated at reflux for 15 minutes. The mixture was cooled, poured into 500 ml water and filtered to yield 5.2 g of 2-nitro-4-methyl-5-methoxy aniline.

(c) The product of step (b) (5.2 g, 28 mmol) was combined under nitrogen with 75 ml DMF and 6.5 g (0.30 mmol) 2,3-dichloro-5-trifluoromethyl pyridine. Sodium hydride (1.5 g, 62.5 mmol) was slowly added to the mixture portionwise. The mixture was allowed to stir 2.5 hours at ambient temperature then slowly poured into dilute hydrochloric acid/ice whereupon 9.5 g of 2-nitro-4-methyl-5-methoxy-N-[2'-(3'-chloro-5'-trifluoromethyl)pyridyl] aniline solids were collected.

(d) Iron, (4.3 g, 77.1 mmol) reduced electrolytically 80 ml ethanol, 67.2 ml water and 0.333 ml concentrated hydrochloric acid were combined and heated to reflux. To this mixture, the product of step (c), (9.3 g, 25.7 mmol) was added portionwise at a rate to maintain reflux throughout. The mixture was allowed to reflux 45 minutes, cooled to 60°–65° C., neutralized with 0.333 g, 50% sodium hydroxide, filtered through diatomaceous earth, stripped under vacuum, slurried with water and filtered to yield 7.1 g of 4-methoxy-5-methyl-2-[2'-(3'-chloro-5'-trifluoromethyl)pyridyl]-1,2-phenylene-diamine solids.

(e) The product of step (d) (2.0 g, 6.0 mmol) was combined with 20 ml DMF, 0.89 ml (6.6 mmol) isoamyl nitrite and 3 drops (catalyst) methanesulfonic acid and allowed to stir at ambient temperature overnight. The mixture was stripped under vacuum and the resulting solids were treated with water and the product filtered and dried to yield 1.7 g of 5-methyl-6-methoxy-1-[2'-(3'-chloro-5'-trifluoromethyl pyridyl]1[H]-benzotriazole solids.

EXAMPLE 4

Preparation of 5-fluoro-5-[2'-(3'-chloro-5'-trifluoromethyl)pyridyl]1[H]-benzotriazole (Compound 25 herein)

(a) 2-nitro-4-fluoroaniline (6 g, 38.5 mmol) was combined under nitrogen with 75 ml DMF and 8.3 g (38.5 mmol) 2,3-dichloro-5-trifluoromethyl pyridine. Sodium hydride 1.9 g (80.0 mmol) was added to the mixture slowly and portionwise. The mixture was allowed to stir overnight at ambient temperature then slowly poured into dilute hydrochloric acid/ice whereupon 11.1 g of 2-nitro-4-fluoro-N-[2'-(3'-chloro-5'-tri-fluoromethyl)pyridyl] aniline solids were collected.

(b) Iron (reduced electrolytically) (5.5 g, 98.4 mmol), 100 ml ethanol, 85 ml water and 0.42 ml (catalyst) concentrated hydrochloric acid were combined and heated to reflux. To this mixture were added portionwise the product of step (a) (11 g, 32.8 mmol) at a rate to maintain reflux throughout. The mixture was allowed to reflux 40 minutes, cooled to 60°–65° C. whereupon it was neutralized with 0.42 g 50% sodium hydroxide, filtered through diatomaceous earth, stripped under vacuum, slurried with water and filtered to yield 9.2 g of 5-fluoro-2-[2'-(3'-chloro-5'-trifluoromethyl) pyridyl]-1,2-phenylenediamine solids.

(c) The product of step (b), (2 g, 6.55 mmol) was combined with 20 ml DMF, 0.97 ml (7.2 mmol) isoamyl nitrite and 3 drops (catalyst) methanesulfonic acid and stirred at ambient temperature overnight.

The mixture was stripped under vacuum which resulted in a solid that was treated with water, filtered and dried to yield 2.0 g of 5-fluoro-[2'-(3'-chloro-5'-trifluoromethyl)-pyridyl] 1[H]-benzotriazole solids.

EXAMPLE 5

Preparation of 6-methylthio-1-[2'-(3'-chloro -5'-trifluoromethyl)pyridyl]1[H]-benzotriazole (Compound 29 herein)

(a) 2-nitro-5-chloroaniline (12.9 g, 75 mmol) was combined with 125 ml DMF and 16.2 g (75.0 mmol) 2,3-dichloro-5-trifluoromethyl pyridine under nitrogen. Sodium hydride (3.0 g, 130 mmol) was added portionwise and slowly the mixture was allowed to stir at ambient temperature. Sodium hydride (0.8 g, 35 mmol) was added the following morning and the mixture was allowed to stir 1.5 hours at ambient temperature, then slowly was poured into dilute hydrochloric acid/ice whereupon 23.9 g of 2-nitro-5-chloro-N-[2'-(3'-chloro-5-tri-fluoromethyl)pyridyl] aniline solids were collected.

(b) The product of step (a), (3.5 g, 10 mmol) was combined with 30 ml DMF and 0.8 g (11 mmol) sodium methane-thioate and heated to 70° C. for one minute, then stirred at ambient temperature one hour, poured into water whereupon 3.5 g of 2-nitro-5-thiomethyl-N-[2'-(3'-chloro-5-trifluoromethyl-pyridyl] aniline solids were collected.

(c) Iron (electrolytically reduced) (1.62 g, 29 mmol), 50 ml ethanol, 42.5 ml water and 0.12 ml concentrated hydrochloric acid were combined and heated to reflux. To this mixture were added portionwise 3.5 g (9.63 mmol) 4-methyl thio-2-nitro-N-[2'-(3'-chloro-5-trifluoromethyl)pyridyl] aniline at a rate to maintain reflux throughout. The mixture was allowed to reflux one hour, cooled to 60°–65° C. whereupon it was neutralized with 0.12 g 50% sodium hydroxide, filtered through diatomaceous earth, stripped under vacuum, slurried with water and filtered to yield 3.0 g of 4-methylthio-2-[2'-(3'-chloro-5-trifluoromethyl) pyridyl]-1,2-phenylenediamine solids.

(d) The product of step (c), (3.0 g, 9 mmol) was combined with 30 ml dimethylformamide, 1.33 ml (9.9 mmol) isoamyl nitrite and 4 drops methanesulfonic acid and allowed to stir one hour at ambient temperature. The mixture was stripped under vacuum then extracted with diethyl ether, treated with water. The organics were dried over magnesium sulfate and stripped under vacuum to yield 2.5 g of 6-methyl-thio-1-[2'-(3'-chloro-5'-trifluoromethyl)pyridyl]1[H]-benzotriazole solids.

EXAMPLE 6

Preparation of 6-dimethylamino-1-[2'-(3'-chloro-5'-trifluoromethyl)pyridyl]1[H]-benzotriazole (Compound 32 herein)

(a) 5-chloro-2-nitro-N-[2'-(3'-chloro-5'-trifluoro-methyl) pyridyl] aniline (3.5 g, 10 mmol) was combined with 30 ml DMF, 5 g (44 mmol) dimethylamine (40% in water), heated at reflux 4 hours, cooled to ambient temperature, then poured into water whereupon 3.3 g of 5-dimethylamino-2-nitro-N-[2'-(3'-chloro-5'-trifluoromethyl)pyridyl] aniline solids were collected.

(b) Iron (electrolytically reduced), (1.62 g, 29 mmol) 50 ml ethanol, 42.5 ml water and 0.12 ml concentrated hydrochloric acid were combined and heated to reflux. The product of step (a) (3.3 g, 9.2 mmol) was added portionwise at a rate to maintain reflux throughout. The mixture was allowed to reflux 0.5 hour, cooled to 60°–65° C., neutralized with 0.12 g 50% sodium hydroxide, filtered through diamtomaceous earth, stripped under vacuum, slurried with water and filtered to yield 2.7 g of 5-dimethylamino-2-[2'-(3'-chloro-5'trifluoro-methyl)pyridyl]-1,2-phenylenediamine solids.

(c) The product of step (b) (2.7 g, 8.2 mmol) was combined with 20 ml DMF, 1.33 ml (9.9 mmol) isoamyl nitrite and 3 drops (catalyst) methanesulfonic acid and allowed to stir at ambient temperature one hour. The mixture was stripped under vacuum, extracted with diethyl ether, treated with water, the organics dried over magnesium sulfate and stripped under vacuum to yield 2.5 g of 6-dimethylamino-1-[2'-(3'-chloro-5'trifluoromethyl)pyridyl] 1[H]-benzotriazole solids.

EXAMPLE 7

Preparation of 5-carbomethoxy-6-methoxy-1-[2'-(3'-chloro-5'-trifluoromethyl)pyridyl]1[H]-benzotriazole (Compound 44 herein)

(a) 4-amino salicylic acid (30.6 g, 200 mmol), 300 ml acetone and 24 g potassium hydroxide (KOH) were combined and allowed to stir at ambient temperature overnight. Dimethyl sulfate (57 g, 450 mmol) was added to the mixture dropwise rapidly and allowed to stir one hour at ambient temperature. Gas-liquid phase chromatography showed the reaction to be incomplete so 5 g additional KOH was added and the mixture was stirred one additional hour, stripped under vacuum, combined with 150 ml water, and extracted liberally with dichloromethane. The solution was dried over magnesium sulfate then stripped under vacuum to yield 50 g of a crude material which was triturated with ether and yielded 15.8 g of 4-carbomethoxy-5-methoxyaniline solids.

(b) The product of step (a) (15.8 g, 87 mmol) 15 ml acetic anhydride (100 mmol) and 15 ml acetic acid were combined and allowed to exotherm, stirred at ambient temperature one hour then stripped under vacuum. The residue was added to a solution of 20 ml (320 mmol) concentrated nitric acid and 15 ml concentrated sulfuric acid, cooled in an ice bath, stirred several hours then poured into water. The resulting solids were washed liberally with water, charged into a flask with 100 ml concentrated hydrochloric acid, heated just to reflux, cooled and stripped. Methanol (100 ml) was added to the resulting residue. The mixture was refluxed 2 hours and stripped under vacuum. Sodium hydroxide (50 ml, 1M) were added to the flask following stripping, then extracted liberally with dichloromethane, the organics dried over magnesium sulfate and stripped under vacuum to yield 2.2 g of impure product.

(c) The product of step (b) was combined with 25 ml DMF and 2.1 g (10.0 mmol) 2,3-dichloro-5-trifluoromethyl pyridine under nitrogen. Sodium hydride (5 g, 21.0 mmol) was added slowly portionwise and the mixture allowed to stir overnight at ambient temperature. The mixture was poured slowly into ice water whereupon 3.5 g of 4-carbomethoxy-5-carboxy-2-nitro-N-[2'-(3'-chloro-5'-trifluoromethyl)pyridyl] aniline solids were collected.

(d) Iron (reduced electrolytically) (4 g, 70 mmol), 80 ml ethanol, 50 ml water and 0.2 ml (catalyst) were combined and heated to reflux. To this mixture was added portionwise 3 g (7.5 mmol) 4-carbomethoxy-5-carboxy-2-nitro-N-[2'-(3'-chloro-5-trifluoromethyl)pyridyl] aniline at a rate to maintain reflux throughout. The mixture was allowed to reflux 6 hours and cooled to 60°–65° C. The mixture was neutralized with 0.2 g 50% NaOH, stripped, extracted with dichloromethane and treated with water. The organics were dried over magnesium sulfate and stripped to yield 0.8 g 4-carboxymethyl-5-carboxy-2-[2'-(3'-chloro-5'-trifluormethyl)pyridyl-1,2-phenylene-diamine residue.

(e) All of the product of step (d) was combined with 10 ml DMF, a small quantity of isoamyl nitrite and a few drops of methanesulfonic acid and allowed to stir at ambient temperature overnight. The mixture was stripped, extracted with diethyl ether, treated with water and then 5% potassium carbonate. The organics were dried over magnesium sulfate and stripped to yield solids which were triturated with a mixture of diethyl ether and pentanes to yield 0.15 g of 5-carbo-methoxy-6-methoxy-1-[2'(3'-chloro-5'trifluoromethyl)pyridyl]-1[H]-benzotriazole solids.

EXAMPLE 8

Preparation of 5-chloro-6-(pentamethylene)amino-1-2' (3'-chloro-5'-trifluoromethy)pyridyl]1[H]-benzotriazole (Compound 48 herein)

(a) 4,5 dichloro-2-nitroaniline, (15 g, 72.5 mmol), 315 ml DMF and 15.66 g (72.5 mmol) 2,3-dichloro-5-trifluoromethyl pyridine were combined under nitrogen. Sodium hydride 3.8 g (159 mmol) was added portionwise and slowly. The mixture was allowed to stir overnight at ambient temperature and then was slowly poured over dilute hydrochloric acid/ice whereupon 26.1 g of 2-nitro-4,5-dichloro-N-[2'-(3'-chloro-5'-trifluoromethyl)pyridyl] aniline solids were collected.

(b) The product of step (a) (3 g, 7.76 mmol) and 7 ml (excess) piperidine were combined neat, heated just to reflux. Dilute hydrochloric acid was added to the mixture and the product filtered off to yield 3.2 g of 2-nitro-4-chloro-5-(pentamethylene)amino-N-[2'-(3'-chloro-5'-trifluoromethyl)pyridyl] aniline solids.

(c) Iron (reduced electrolytically) (1.3 g, 22.8 mmol), 40 ml ethanol, 35 ml water and 0.1 ml (catalyst) concentrated hydrochloric acid were combined and brought to reflux. The product of step (b) was added portionwise to this mixture (3.2 g, 7.4 mmol) at a rate to maintain reflux throughout. The mixture was allowed to reflux 1.5 hours, cooled to 60°–65° C. whereupon it was neutralized with 0.1 g 50% sodium hydroxide, filtered through diatomaceous earth, stripped under vacuum, slurried with water and filtered to yield 2.5 g of 4-chloro-5-(pentamethylene)amino-1-[2'-(3'-chloro-5'-tri-fluoromethyl)pyridyl]-1,2-phenylenediamine solids.

(d) The product of step (c) (2.5 g, 6.2 mmol), 25 ml DMF, 0.92 ml (6.8 mmol) isoamyl nitrite and a few drops (catalyst) methanesulfonic acid were combined and allowed to stir at ambient temperature overnight. The mixture was stripped to dryness under vacuum, extracted with diethyl ether, treated with water and separated. The organics were dried over magnesium sulfate and stripped to yield 2.0 g of 5-chloro-6-(pentamethylene)amino-1-[2'-(3'-chloro-5'-tri-fluoromethyl)pyridyl]1[H]-benzotriazole solids.

EXAMPLE 9

Preparation of 5-chloro-6-(N-methyl-N-carboxymethyl)amino-1-[2'-(3'-chloro-5-trifluoromethyl)-pyridyl]1[H]-benzotriazole (Compound 49 herein)

(a) 2-nitro-4,5-dichloro-N-[2'-(3'-chloro-5'-trifluoromethyl)pyridyl] aniline, (3.0 g, 7.76 mmol), 20 ml 1-methyl-2-pyrrolidinone, 0.8 g (9.0 mmol) sarcosine and 2 g (0.019 mmol) triethylamine were combined and heated at 85°–100° C. for 2.5 days. The mixture was cooled to ambient temperature. Dilute caustic was added and the mixture was treated with diethyl ether and phase separated. The caustic solution was acidified to yield 1.4 g of 2-nitro-4-chloro-(N'-methyl-N'-carboxymethyl)amino-N-[2"-(3"-chloro-5"-tri-fluoromethyl)pyridyl] aniline solids.

(b) Iron (reduced electrolytically) (2.3 g, 40 mmol), 40 ml ethanol, 10 ml water and 0.2 ml concentrated hydrochloric acid were combined and heated to reflux. The product of step (a), (2.7 g, 6 mmol), was added portionwise at a rate to maintain reflux throughout. The mixture was allowed to reflux 3 hours, cooled to 60°–65° C., neutralized with 0.2 ml 50% NaOH and filtered through diatomaceous earth. The mixture was further stripped under vacuum, extracted liberally with dichloromethane, the organics washed with dilute hydrochloric acid and separated. The organics were dried over magnesium sulfate and stripped to yield 1.2 g of 5-chloro-4-(N'-methyl-N'carboxymethyl)amino-2-[2'-(3'-chloro-5'-trifluoromethyl)-pyridyl]-1,2-phenylenediamine product.

(c) The product of step (b) (1.2 g, 3.0 mmol), was combined with 10 ml DMF, 0.4 g (3.4 mmol) isoamyl nitrite and one drop (catalyst) methanesulfonic acid and allowed to stir at ambient temperature overnight. The mixture was stripped, extracted with diethyl ether and treated with water. The organics were dried over magnesium sulfate and stripped to yield 1.2 g impure product.

The impure product was dissolved in diethyl ether and extracted with dilute sodium hydroxide. The caustic layer was acidified and extracted with dichloromethane which was dried over magnesium sulfate and stripped under vacuum to yield 0.5 g of 5-chloro-6-(N-methyl-N-carboxymethyl)amino-1-[2'-(3'-chloro-5-trifluoromethyl)pyridyl]1[H]-benzotriazole solids.

EXAMPLE 10

Preparation of 5-fluoro-6-(1'-carboxmethoxy)ethoxy-1-[2"-(3"-chloro-5"-trifluoromethyl)pyridyl]1[H]-benzotriazole (Compound 51 herein)

(a) 2,5-difluorophenol (20 g, 15.4 mmol) was dissolved in 50 ml methylene chloride with stirring. 11 ml (176.0 mmol) concentrated nitric acid was added dropwise and the mixture was cooled in an ice bath. The mixture was phase separated. The organics were dried over magnesium sulfate and stripped to yield 27 g product which was triturated with 10% benzene in hexanes to yield 14.4 g of 2,5-difluoro-4-nitro-phenol solids.

(b) The product of step (a) (3.4 g, 20 mmol), 50 ml acetonitrile, 3.3 g potassium carbonate and 3 g allyl bromide were combined, heated to reflux for one hour and stripped. The mixture was extracted with dichloromethane, treated with water and separated. The organics were dried over magnesium sulfate and stripped to yield 1.9 g of 4-allyloxy-2,5 difluoro nitrobenzene product.

(c) The product of step (b) (1.9 g, 9.0 mmol), 20 ml DMF and 1.8 g (9.0 mmol) 2-amino-3-chloro-5-trifluoromethyl pyridine were combined under nitrogen. Sodium hydride (0.5 g, 21.0 mmol) was added to the mixture slowly and portionwise. The mixture was allowed to stir overnight at ambient temperature. Water was added to the mixture to produce 2.5 g solids which were triturated with a 50:50 solution of diethyl ether: pentanes to produce 4-fluoro-5-allyloxy-2-nitro-1 [2'-(3'-chloro-5'-trifluoromethyl)pyridyl] aniline solids.

(d) Iron powder (reduced electrolytically) (2 g, 33.0 mmol), 25 ml ethanol, 7 ml water and 0.2 ml (catalyst) concentrated hydrochloric acid were combined and heated to reflux. The product of step (c), (1.4 g, 3.6 mmol), was added portionwise to the above mixture at a rate to maintain reflux throughout. The mixture was allowed to reflux 3 hours after the addition was complete, then cooled to 60°–65° C. whereupon it was neutralized with 0.2 g 50% sodium hydroxide. The mixture was filtered through diatomaceous earth, stripped under vacuum, extracted with diethyl ether, treated with water and separated. The organics were dried over magnesium sulfate and stripped under vacuum to yield 1.3 g of 4-fluoro-5-allyloxy-1[2'-)3'-chloro-5-trifluoromethyl)pyridyl]-1,2-phenylene-diamine product.

(e) The product of step (d), (1.3 g, 3.6 mmol), 10 ml DMF, 0.5 g (4.0 mmol) isoamyl nitrite and 2 drops (catalyst) methanesulfonic acid were combined and stirred overnight at ambient temperature. The mixture was stripped, extracted with diethyl ether, treated with water and separated. The organics dried over magnesium sulfate and stripped to yield 1 g of 5-fluoro-6-allyloxy-1-[2'-(3'-chloro-5'-trifluoromethyl)-pyridyl]1[H]-benzotriazole product.

(f) The product of step (e) (1 g, 2.7 mmol), 10 ml tetrahydrofuran, 0.3 g (3.0 mmol) triethylamine and a catalytic amount of palladium acetate were combined and heated to reflux. Formic acid (0.2 g, 4.0 mmol) was added to the mixture which was allowed to reflux 1.5 hours. The mixture was stripped, extracted with diethyl ether, treated with water and separated. The organics were dried over magnesium sulfate and stripped to yield 0.7 g of 5-fluoro-6-hydroxy-1-[2'-(3'-chloro-5'-trifluoromethyl)pyridyl]1[H]-benzotriazole product.

(g) The product of step (f) (0.7 g, 2.1 mmol), 10 ml acetonitrile, 0.4 g (2.4 mmol) methyl-2-bromopropionate and 0.4 g (2.8 mmol) powdered potassium carbonate were combined and heated at reflux one hour. The mixture was stripped, extracted with dichloromethane, treated with water and separated. The organics were dried over magnesium sulfate and stripped to yield 0.8 g of 5-fluoro-6-(1'-carbomethoxy)ethoxy-1-[2"-(3"-chloro-5"-trifluoromethyl)pyridyl]1[H]-benzotriazole semi-solid material.

EXAMPLE 11

Preparation of 5-chloro-6-(1'-carbomethoxy)ethoxy-1-[2"-(3"-chloro-5"-trifluoromethyl)pyridyl]-1[H]-benzotriazole (Compound 110 herein)

(a) 2,5-dichlorophenol (72 g, 440 mmol) were slurried in 100 ml dichloromethane which resulted in an endothermic reaction. To this mixture were slowly added 30 ml (480 mmol) concentrated nitric acid. The reaction was allowed to reach and maintain reflux. The mixture was stirred until it reached ambient temperature and all materials remained in solution. 50 g of ice were added and solids precipitated. The mixture was filtered cold and washed with 25 ml dichloromethane, 50 ml dichloromethane, then twice with 25 ml dichloromethane to yield 28.4 g of 2,5-dichloro-4-nitrophenol.

(b) The product of step (a) (59.3 g, 285 mmol), 550 ml acetonitrile, 43 g (314 mmol) of potassium carbonate and 27.2 ml (314 mmol) of allyl bromide were combined and heated to reflux, and then the reaction was evaporated under reduced pressure. The mixture was extracted with diethyl ether, washed with water, and separated. The organics were dried over magnesium sulfate and stripped to yield 66.1 g of 4-allyloxy-2,5-dichloronitrobenzene product.

(c) The product of step (b) (66.1 g, 267 mmol) was dissolved in 600 ml DMF at ambient temperature. Sodium azide (19.1 g, 267 mmol) was added and the mixture allowed to stir over a 4-day weekend, after which another 2 g (30.8 mmol) of the azide were added. Sodium borohydride (2.77 g, 73.5 mmol) was added in small portions while cooling in an ice bath. The mixture was stirred over night and then another 0.85 g (0.015 m) of sodium borohydride were added portionwise to the cold mixture. When the reaction appeared complete, the mixture was poured over ice water, the product filtered and dried to yield 50.5 g of 2-nitro-4-chloro-5-allyloxyaniline.

(d) The product of step (c) (25.3 g, 111 mmol) was combined in DMF with 2,3-dichloro-5-trifluoromethylpyridine (23.9 g, 111 mmol). Sodium hydride (5 g, 243 mmol) was added portionwise, under a blanket of nitrogen (N₂) at a rate to maintain the temperature below 30° C. When the reaction was complete, the mixture was carefully poured into ice water, filtered and dried to yield 38.2 g of 4-chloro-5-allyloxy-2-nitro-1-[2'-(3'-chloro-5'-trifluoromethyl)pyridyl]aniline.

(e) Iron powder (reduced electrolytically) (16.5 g, 300 mmol), 350 ml ethanol, 70 ml water, and 3.4 ml (41 mmol) concentrated hydrochloric acid were combined and heated to reflux. The product of step (d) (38.2 g, 104 mmol) was added portionwise at a rate to maintain reflux. Reflux was maintained until no more starting material was present. The mixture was filtered hot thourgh diatomacious earth and stripped to dryness. The resulting mixture was combined with 350 ml DMF and 13.9 ml (104 mmol) isoamyl nitrite and 3 drops (catalytic) methane sulfonic acid were added. The mixture was allowed to stir over a weekend, stripped, extracted with dichloromethane dried and stripped. The mixture was then put through a silica gel column, eluted with ethyl acetate and stripped to yield 28.6 g of 5-chloro-6-allyloxy-1-[2'-(3'-chloro-5'-trifluoromethyl) pyridyl]1[H]-benzotriazole product.

(f) The product of step (e) (21.7 g, 56 mmol), 210 ml tetrahydrofuran, 7.9 g (57 mmol) triethylamine and 1.26 g (5.6 mmol) palladium II acetate were combined and heated to reflux. Formic acid (4.2 ml, 112 mmole) was added dropwise while reflux was maintained. The mixture was filtered to remove any solids, stripped, extracted with dichloromethane, washed with water, and the mixture again filtered to remove insoluble solid product which were dried to yield 13.7 g 5-chloro-6-hydroxy-1-[2'-(3'-chloro-5'-trifluoromethyl)pyridyl]-1[H]-benzotriazole.

(g) The product of step (f) (20 g, 57.3 mmol) was combined with 200 ml acetonitrile, 11 g (60.2 mmol) S-(-)-methyl-2-methylsulfonyl proprionate and 8.4 g (60.7 mmol) potassium carbonate and refluxed one hour until the reaction was complete. The mixture was filtered to remove any solids, evaporated under reduced pressure, extracted with dichloromethane and water, and the organic phase dried and stripped. The mixture was put through a silica gel column, and eluted with ethylacetate to yield 21.7 g of 5-chloro-6-(1'-carbo-methoxy)ethoxy-2-[2"-(3"-chloro-5"-trifluoromethyl)pyridyl]-1[H]-benzotriazole.

EXAMPLE 12

Preparation of 5-trifluoromethyl-6-(S-methylsulfonyl)amino-1-[2',6'-dichloro-4'-trifluoromethyl)phenyl]-1[H]-benzotriazole (Compound 98 herein)

(a) 2,4-dichloro-5-nitrobenzotrifluoride (5.2 g., 20 mmol), 90 ml DMF and 4.6 g (20 mmol) 4-amino-3,5-dichlorobenzotrifluoride were combined under nitrogen gas at room temperature. Sodium hydride (1 g, 41 mmol) was added slowly and portionwise at a rate to keep the temperature under 30° C. When starting materials were no longer present, the mixture was poured over ice to which a small amount of dilute HCl was added. The ice mixture was allowed to melt and the solid product filtered off and dried to yield 8.2 g.

(b) The product of step (a) (7 g, 16.5 mmol) was combined with sodium azide (1.12 g, 17.2 mmol) and 25 ml of DMF. The mixture was heated at 60° C. for one hour until no starting material remained. Isopropanol (100 ml) was added all at once, then sodium borohydride (0.6 g, 2.5 mmol) was added portionwise and slowly. The mixture was again heated to 60° C. for an hour until the reaction was complete. Water (2 ml) was added dropwise, followed by an additional 150 ml of water. The mixture was stirred for one-half hour, the product filtered off and dried to yield 5.4 g. (c) The product of step (b) (5.4 g, 13.5 mmol) was added portionwise and slowly to 1.3 g (25 mmol) 20% phosgene in toluene and 60 ml ethyl acetate. The mixture was heated at reflux for one hour, then evaporated under reduced pressure. Dichloromethane (50 ml), 1.2 g (213 mmol) allylalcohol, and 2 drops (cat) of triethylamine were added to the resulting intermediate and the mixture allowed to stir overnight. The product was evaporated under reduced pressure to yield 6.4 g.

(d) Iron powder (reduced electrolytically)(2.22 g, 39.6 mmol), 100 ml ethanol, 80 ml water, and 1.2 ml (2.06 mmol) concentrated hydrochloric acid were combined and heated to reflux. The product of step (c) (6.4 g, 13.2 mmol) was added portionwise while maintaining reflux. When no starting material remained, the iron oxides were filtered off and the mixture evaporated to dryness. The resulting mixture was combined with 50 ml DMF, 2.05 ml (14.8 mmol) isoamyl nitrite and 2 drops (catalytic) methanesulfonic acid and allowed to stir over a weekend. The mixture was evaporated to dryness, dissolved in diethyl ether, washed with water, the organics dried over magnesium sulfate, and evaporated to yield 5.6 g.

(e) The product of step (d) (5.6 g, 12.0 mmol) was combined with 45 ml THF, 1.84 ml (13.2 mmol) triethylamine and 0.26 g palladium II acetate and heated to reflux. Formic acid (1.2 ml, 25.2 mmol) was added dropwise to the refluxing mixture. When reaction was complete, the mixture was evaporated to dryness, extracted with diethylether, washed with water, the organics dried over magnesium sulfate and evaporated to yield 3.9 g.

(f) The product of step (e) (1.0 g, 2.62 mmol) was combined with 10 ml ethylene dichloride, 0.5 ml (3.93 mmol) N,N-dimethylaniline and 0.68 g (3.93 mmol) methanesulfonic anhydride, evaporated under reduced pressure and heated to 70° C. When the reaction was complete, the mixture was exracted into dichloromethane, washed with water, the organics dried over magnesium sulfate and evaporated to dryness to yield 1.1 g of crude product which was eluted with ethylacetate on a silica gel column to yield 0.55 g of purified product.

The structure of the final product for each step of each example was confirmed by infrared spectroscopy, mass spectrometry and nuclear magnetic resonance spectroscopy.

Table I depicts representative compounds of this invention, prepared by a process as described above.

TABLE I

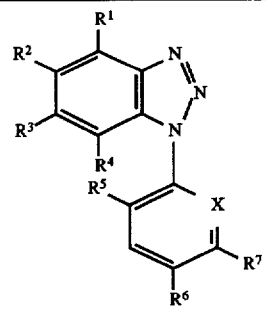

| CMPD. NO. | $R^1$ | $R^2$ | $R^3$ | $R^4$ | $R^5$ | $R^6$ | $R^7$ | X | Physical Constant M.P. °C. |
|---|---|---|---|---|---|---|---|---|---|
| 1 | H | $NO_2$ | H | H | Cl | $CF_3$ | H | C—Cl | — |
| 2 | H | $CH_3$ | $CH_3$ | H | Cl | $CF_3$ | H | (N) | 148.0–150.0 |
| 3 | H | H | H | H | Cl | $CF_3$ | H | (N) | 78.0–79.0 |
| 4 | H | H | H | H | Cl | $CF_3$ | H | C—Cl | 116.0–119.0 |
| 5 | H | Cl | H | H | Cl | $CF_3$ | H | (N) | 143.0–145.0 |
| 6 | H | H | Cl | H | Cl | $CF_3$ | H | (N) | 99.0–102.0 |
| 7 | H | Cl | H | H | Cl | $CF_3$ | H | C—Cl | 133.0–135.0 |
| 8 | H | H | Cl | H | Cl | $CF_3$ | H | C—Cl | 129.0–130.0 |
| 9 | H | H | $CH_3$ | H | Cl | $CF_3$ | H | (N) | 74.0–77.0 |
| 10 | H | $CH_3$ | H | H | Cl | $CF_3$ | H | C—Cl | 78.0–82.0 |
| 11 | H | $CO_2C_2H_5$ | H | H | Cl | $CF_3$ | H | C—Cl | — |
| 12 | H | $CO_2CH_3$ | H | H | Cl | $CF_3$ | H | C—Cl | — |
| 13 | H | H | $OCH_3$ | H | Cl | $CF_3$ | H | (N) | 101.6–103.0 |
| 14 | H | H | OCH(CH₃)—C(=O)—OCH₃ | H | Cl | $CF_3$ | H | (N) | 94.5–96.4 |
| 15 | H | H | OH | H | Cl | $CF_3$ | H | (N) | 127.5–130.3 |
| 16 | H | H | $OCH_2CN$ | H | Cl | $CF_3$ | H | (N) | 102.4–109.5 |
| 17 | H | H | $OCH_2C{\equiv}CH$ | H | Cl | $CF_3$ | H | (N) | 105.6–107.0 |
| 18 | H | H | $OCH_2CH{=}CH_2$ | H | Cl | $CF_3$ | H | (N) | 89.6–90.5 |
| 19 | H | H | $OCH_2CCl{=}CH_2$ | H | Cl | $CF_3$ | H | (N) | 49.0–50.4 |
| 20 | H | $CF_3$ | H | H | Cl | $CF_3$ | H | (N) | 95.0–96.8 |
| 21 | H | $CH_3$ | $OCH_3$ | H | Cl | $CF_3$ | H | (N) | 158.8–160.0 |
| 22 | H | H | OCH(CH₃)—C(=O)—O | H | Cl | $CF_3$ | H | (N) | 195.8–198.2 |
| 23 | H | F | $OC_2H_5$ | H | Cl | $CF_3$ | H | (N) | 110.0–113.3 |
| 24 | H | F | Cl | H | Cl | $CF_3$ | H | (N) | 122.8–124.2 |

TABLE I-continued

| CMPD. NO. | R¹ | R² | R³ | R⁴ | R⁵ | R⁶ | R⁷ | X | Physical Constant M.P. °C. |
|---|---|---|---|---|---|---|---|---|---|
| 25 | H | F | H | H | Cl | $CF_3$ | H | (N) | 78.9–80.3 |
| 26 | $CF_3$ | H | H | H | Cl | $CF_3$ | H | (N) | 120.8–122.4 |
| 27 | H | Cl | Cl | H | Cl | $CF_3$ | H | (N) | 133.5–135.0 |
| 28 | H | H | $OCH_2C(=O)OC_2H_5$ | H | Cl | $CF_3$ | H | (N) | — |
| 29 | H | H | $SCH_3$ | H | Cl | $CF_3$ | H | (N) | 107.4–112.0 |
| 30 | H | H | $SCH(CH_3)C(=O)OC_2H_5$ | H | Cl | $CF_3$ | H | (N) | — |
| 31 | H | H | $SCH_2C(=O)OC_2H_5$ | H | Cl | $CF_3$ | H | (N) | — |
| 32 | H | H | $N(CH_3)_2$ | H | Cl | $CF_3$ | H | (N) | 103.0–105.0 |
| 33 | H | H | $OCF_3$ | H | Cl | $CF_3$ | H | (N) | 93.4–95.7 |
| 34 | H | H | $CF_3$ | H | Cl | $CF_3$ | H | (N) | 81.4–84.7 |
| 35 | H | Cl | $N(CH_3)_2$ | H | Cl | $CF_3$ | H | (N) | — |
| 36 | H | Cl | $SCH(CH_3)C(=O)OC_2H_5$ | H | Cl | $CF_3$ | H | (N) | 90.9–92.5 |
| 37 | H | Cl | $SCH_2C(=O)OC_2H_5$ | H | Cl | $CF_3$ | H | (N) | 91.9–94.4 |
| 38 | H | H | $N(CH_3)C(=O)OC_2H_5$ | H | Cl | $CF_3$ | H | (N) | — |
| 39 | $CH_3$ | H | H | H | Cl | $CF_3$ | H | (N) | — |
| 40 | H | H | $OCH_2CH=CHCl$ | H | Cl | $CF_3$ | H | (N) | — |
| 41 | H | F | $CH_3$ | H | Cl | $CF_3$ | H | (N) | 95.4–96.0 |
| 42 | H | Cl | $-S(=O)CH(CH_3)C(OC_2H_5)$ | H | Cl | $CF_3$ | H | (N) | — |
| 43 | H | Cl | $-SO_2CH(CH_3)C(=O)C_2H_5$ | H | Cl | $CF_3$ | H | (N) | 109.0–113.0 |
| 44 | H | $CO_2CH_3$ | $OCH_3$ | H | Cl | $CF_3$ | H | (N) | 132.5–136.0 |
| 45 | H | Cl | morpholin-N-yl | H | Cl | $CF_3$ | H | (N) | 164.8–167.4 |
| 46 | H | Cl | piperidin-N-yl | H | Cl | $CF_3$ | H | (N) | 118.1–121.5 |

TABLE I-continued

| CMPD. NO. | R¹ | R² | R³ | R⁴ | R⁵ | R⁶ | R⁷ | X | Physical Constant M.P. °C. |
|---|---|---|---|---|---|---|---|---|---|
| 47 | H | Cl | —N⟨ ⟩S (morpholine-like with S) | H | Cl | CF₃ | H | (N) | — |
| 48 | H | Cl | —N⟨ ⟩ (piperidine) | H | Cl | CF₃ | H | (N) | 101.9–104.3 |
| 49 | H | Cl | NCH₂CO₂H / CH₃ | H | Cl | CF₃ | H | (N) | 67.5–75.5 |
| 50 | H | SO₃H | H | H | Cl | CF₃ | H | (N) | >250.0 |
| 51 | H | F | OCH(CH₃)—C(=O)—OCH₃ | H | Cl | CF₃ | H | (N) | Semi-solid |
| 52 | H | Cl | —N⟨ ⟩NCH₃ (piperazine) | H | Cl | CF₃ | H | (N) | Semi-solid |
| 53 | H | Cl | —N⟨ ⟩NCH₃ (homopiperazine) | H | Cl | CF₃ | H | (N) | Glass |
| 54 | H | F | SCH(CH₃)—C(=O)—OC₂H₅ | H | Cl | CF₃ | H | (N) | Thick oil |
| 55 | H | Cl | SCH₃ | H | Cl | CF₃ | H | (N) | 123.5–131.9 |
| 56 | H | F | S(=O)—CH(CH₃)C(=O)—OC₂H₅ | H | Cl | CF₃ | H | (N) | Thick oil |
| 57 | H | F | SO₂CH(CH₃)—C(=O)—OC₂H₅ | H | Cl | CF₃ | H | (N) | Thick oil |
| 58 | H | Cl | SOCH₃ | H | Cl | CF₃ | H | (N) | 124.7–128.6 |
| 59 | H | Cl | SO₂CH₃ | H | Cl | CF₃ | H | (N) | 141.9–147.2 |
| 60 | H | H | CF₃ | H | Cl | CF₃ | H | (N) | 92.6–95.7 |
| 61 | H | F | —N(CH₃)₂ | H | Cl | CF₃ | H | (N) | 119.0–121.1 |
| 62 | H | F | —N⟨ ⟩O (morpholine) | H | Cl | CF₃ | H | (N) | 150.1–152.3 |
| 63 | H | F | OCH₂CH=CH | H | Cl | CF₃ | H | (N) | 100.4–101.5 |
| 64 | H | F | OCH₂C≡CH | H | Cl | CF₃ | H | (N) | 134.0–137.0 |
| 65 | H | F | OCH₃ | H | Cl | CF₃ | H | (N) | 83.0–89.0 |
| 66 | H | F | OCH₂CN | H | Cl | CF₃ | H | (N) | 120.0–125.0 |

TABLE I-continued

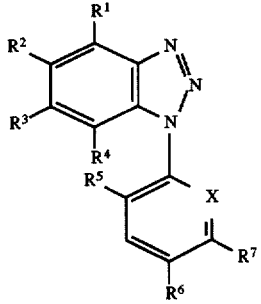

| CMPD. NO. | R¹ | R² | R³ | R⁴ | R⁵ | R⁶ | R⁷ | X | Physical Constant M.P. °C. |
|---|---|---|---|---|---|---|---|---|---|
| 67 | H | Cl | OCH₃ | H | Cl | CF₃ | H | (N) | 154.6–157.1 |
| 68 | H | Cl | R 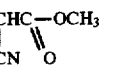 | H | Cl | CF₃ | H | (N) | 191.7–195.4 |
| 69 | H | Cl | S 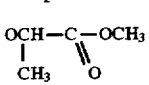 | H | Cl | CF₃ | H | (N) | — |
| 70 | H | Cl | 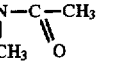 | H | Cl | CF₃ | H | (N) | 144.9–149.5 |
| 71 | H | CH₃ | OCH₂CH=CH₂ | H | Cl | CF₃ | H | (N) | — |
| 72 | H | Cl | CHC—OCH₃ \| \|\| CN  O | H | Cl | CF₃ | H | (N) | — |
| 73 | H | CH₃ | OCH₂ C CH | H | Cl | CF₃ | H | (N) | 136.8–139.7 |
| 74 | H | CH₃ | OCH₂ C N | H | Cl | CF₃ | H | (N) | 149.5–151.6 |
| 75 | H | CH₃ | OCH—C—OCH₃ \| \|\| CH₃  O | H | Cl | CF₃ | H | (N) | 101.9–106.3 |
| 76 | H | Cl | NHCH₃ | H | Cl | CF₃ | H | (N) | 126.0–138.2 |
| 77 | H | Cl | N—C—CH₃ \| \|\| CH₃ O | H | Cl | CF₃ | H | (N) | 137.4–147.8 |
| 78 | H | Cl | NHCH₂C—OC₂H₅ \|\| O | H | Cl | CF₃ | H | (N) | 113.0–118.6 |
| 79 | H | CF₃ | 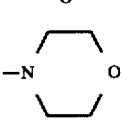 | H | Cl | CF₃ | H | C—Cl | 183.8 to 185.1 |
| 80 | H | CN | NHCH—C—OC₂H₅ / \|\| CH₃ O | H | Cl | CF₃ | H | C—Cl | — |
| 81 | H | CF₃ | NHCH—C—OC₂H₅ / \|\| CH₃ O | H | Cl | CF₃ | H | C—Cl | 73.6–77.8 |
| 82 | H | CF₃ | NHCH—C—OC₂H₅ / \|\| CH₃ O | H | H | CF₃ | H | C—Cl | 118.8–120.2 |
| 83 | H | CF₃ | Cl | H | Cl | CF₃ | H | C—Cl | 121.8–124.1 |

TABLE I-continued

[Structure: benzotriazole with R1, R2, R3, R4 on benzene ring, N-substituted with phenyl ring bearing R5, R6, R7 and X]

| CMPD. NO. | R¹ | R² | R³ | R⁴ | R⁵ | R⁶ | R⁷ | X | Physical Constant M.P. °C. |
|---|---|---|---|---|---|---|---|---|---|
| 84 | H | CN | OCH(CH₃)—C(=O)—OC₂H₅ | H | Cl | CF₃ | H | C—Cl | 156.7–157.8 |
| 85 | H | CN | N(CH₃)₂ | H | H | CF₃ | H | C—Cl | 160.2–162.3 |
| 86 | H | CN | NHCH(CH₃)—C(=O)—OC₂H₅ | H | H | CF₃ | H | C—Cl | 162.0 |
| 87 | H | CN | OCH₃ | H | H | CF₃ | H | C—Cl | 142.4–154.4 |
| 88 | H | CN | OCH(CH₃)—C(=O)—OC₂H₅ | H | H | CF₃ | H | C—Cl | 132.8–133.9 |
| 89 | H | CNH₂ | OCH(CH₃)—C(=O)—OH | H | H | CF₃ | H | C—Cl | 223.6–225.3 |
| 90 | H | CN | OCH₂CH=CH | H | H | CF₃ | H | C—Cl | 116.1–118.5 |
| 91 | H | CN | N(CH₃)₂ | H | Cl | CF₃ | H | C—Cl | 154.0–158.0 |
| 92 | H | CN | OCH(CH₃)—C(=O)—OH | H | H | CF₃ | H | C—Cl | 79.6–81.9 |
| 93 | H | CN | OCH₂CH=CH₂ | H | Cl | CF₃ | H | C—Cl | 119.1–121.7 |
| 94 | H | CN | OCH(CH₃)—C(=O)—OCH₃ | H | Cl | CF₃ | H | C—Cl | 64.1–66.6 |
| 95 | H | CN | OCH(CH₃)—C(=O)—OCH₃ | H | Cl | CF₃ | H | C—Cl | — |
| 96 | H | CN | OCH₃ | H | Cl | CF₃ | H | C—Cl | — |
| 97 | H | CN | OCH(CH₃)—C(=O)—OH | H | Cl | CF₃ | H | C—Cl | 156.4–166.0 |
| 98 | H | CF₃ | NHSO₂CH₃ | H | Cl | CF₃ | H | C—Cl | 157.2–158.3 |
| 99 | H | CF₃ | NHSO₂C₂H₅ | H | Cl | CF₃ | H | C—Cl | 127.3–128.5 |
| 100 | H | CF₃ | NHSO₂CH₂C(=O)—OCH₃ | H | Cl | CF₃ | H | C—Cl | — |
| 101 | H | CF₃ | NHSO₂CH₂CH₂CH₃ | H | Cl | CF₃ | H | C—Cl | 127.3–129.0 |
| 102 | H | CN | OCH₂C=CH | H | Cl | CF₃ | H | C—Cl | Glass |
| 103 | H | CN | NHSO₂ CH₃ | H | Cl | CF₃ | H | C—Cl | 221.8–223.8 |
| 104 | H | CN | NHSO₂C₂H₅ | H | Cl | CF₃ | H | C—Cl | 167.8–170.8 |
| 105 | H | CN | NHSO₂CH₂CH₂CH₃ | H | Cl | CF₃ | H | C—Cl | 172.0–173.9 |
| 106 | H | CF₃ | S—(thiadiazolyl) | H | Cl | CF₃ | H | C—Cl | — |

TABLE I-continued

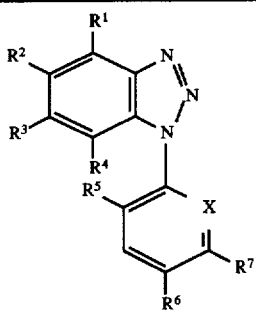

| CMPD. NO. | R¹ | R² | R³ | R⁴ | R⁵ | R⁶ | R⁷ | X | Physical Constant M.P. °C. |
|---|---|---|---|---|---|---|---|---|---|
| 107 | H | CN | OCHC—O—CH₂CH=CH₂<br>  \|       \|\|<br> CH₃    O | H | Cl | CF₃ | H | C—Cl | — |
| 108 | H | CF₃ | NHSO₂CF₃ | H | Cl | CF₃ | H | C—Cl | 131.8–133.5 |
| 109 | H | CF₃ | S—〈N=N〉—CH₂C(=O)—OC₂H₅ | H | Cl | CF₃ | H | C—Cl | 182.0–187.0 |
| 110 | H | Cl | OCHC—OCH₃<br>  \|      \|\|<br> CH₃   O | H | Cl | CF₃ | H | N | 154.0–158.0 |
| 111 | H | CF₃ | NHSO₂CH₃ | H | Cl | CF₃ | H | N | 145.8–147.1 |
| 112 | H | Cl | OCH₂CH=CH₂ | H | Cl | CF₃ | H | C—Cl | 145.0–146.0 |
| 113 | H | Cl | OCHC—OCH₃<br>  \|      \|\|<br> CH₃   O | H | Cl | CF₃ | H | C—Cl | 152.0–154.0 |
| 114 | H | Cl | OCHC—OH<br>  \|      \|\|<br> CH₃   O | H | Cl | CF₃ | H | C—Cl | 195.0–202.0 |
| 115 | H | Cl | OCH₂CH=CH₂ | H | H | CF₃ | H | C—Cl | 129.0–134.0 |
| 116 | H | F | OCH₂CH=CH₂ | H | Cl | CF₃ | H | C—Cl | 106.0–108.0 |
| 117 | H | Cl | OCHC—OCH₃<br>  \|      \|\|<br> CH₃   O | H | H | CF₃ | H | C—Cl | 104.7–106.1 |
| 118 | H | Cl | OCHC—OC₂H₅<br>  \|      \|\|<br> CH₃   O | H | H | CF₃ | H | C—Cl | 79.8–82.6 |
| 119 | H | Cl | OCHC—OC₃H₇<br>  \|      \|\|<br> CH₃   O | H | H | CF₃ | H | C—Cl | Thick oil |
| 120 | H | F | OCHCOCH₃<br>  \|      \|\|<br> CH₃   O | H | Cl | CF₃ | H | C—Cl | 122.6–127.4 |
| 121 | H | F | OCHC—OC₂H₅<br>  \|      \|\|<br> CH₃   O | H | Cl | CF₃ | H | C—Cl | Thick oil |
| 122 | H | F | OCHC—OC₃H₇<br>  \|      \|\|<br> CH₃   O | H | Cl | CF₃ | H | C—Cl | Thick oil |
| 123 | H | F | OCHC—OH<br>  \|      \|\|<br> CH₃   O | H | Cl | CF₃ | H | C—Cl | 145.5–149.1 |

TABLE I-continued

| CMPD. NO. | R¹ | R² | R³ | R⁴ | R⁵ | R⁶ | R⁷ | X | Physical Constant M.P. °C. |
|---|---|---|---|---|---|---|---|---|---|
| 124 | H | Cl | OCHC—OH<br>　│　‖<br>　CH₃ O | H | H | CF₃ | H | C—Cl | 65.9–69.4 |
| 125 | H | Cl | OCH₃ | H | H | CF₃ | H | C—Cl | 139.4–142.3 |
| 126 | H | F | OCH₃ | H | Cl | CF₃ | H | C—Cl | 140.4–142.0 |
| 127 | H | F | OCHC—OCH₃<br>　│　‖<br>　CH₃ O | H | H | CF₃ | H | C—Cl | 126.0–128.6 |
| 128 | H | F | OCH₃ | H | H | CF₃ | H | C—Cl | — |

Herbicidal Screening Tests

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

Pre-Emergence Herbicidal Screening Test

On the day preceding treatment, seeds of several different weed species were planted in sandy loam soil at a depth of 0.5 inch (1.3 cm) in individual rows using one species per row across the width of a flat. The soil was fortified with 17—17—17 fertilizer (N—P₂O₅—K₂O) on a weight basis and pasteurized. The weeds planted were: grasses—green foxtail (*Setaria viridis*), wild oat (*Avena fatua*), and barnyardgrass (*Echinochloa crusgalli*); broadleaf weeds—wild mustard (*Sinapsis arvensis*), velvetleaf (*Abutilon theophrasti*), and annual morningglory (*Ipomoea hederacea*) or morningglory species (*Ipomoea spp.*); and yellow nutsedge (*Cyperus esculentus*). Plant densities ranged from 3 to 25 plants per row, depending upon the size of the plants.

Solutions of the test compounds were made by weighing out 74.7 or 18.8 milligrams (mg) of the test compound into a 60 ml wide-mouth bottle, then dissolving the compound in 7.0 ml acetone containing 1% Tween 20' (polyoxyethylene sorbitan monolaurate emulsifier) and then adding 7 ml of deionized water to reach a 14 ml final volume. Tween 20' content was 0.5% v/v of the final spray volume. Additional solvents, not exceeding 2 ml, were used if needed to dissolve the compound.

The soil surface was sprayed inside an enclosed linear spray table. The flats were sprayed with the spray solution calibrated to deliver 748 L/ha. The application rate was 4.0 or 1.0 kg/ha.

The flats were placed into a greenhouse at 21°–29° C. and water daily by sprinkling. The degree of weed control was visually assessed and recorded 17–21 days after treatment, as percentage control compared to the growth of the same species of the same age in an untreated check flat.

Post-Emergence Herbicidal Evaluation

The soil was prepared and seeded with the same species and methodology described for the pre-emergence test.

The flats were placed in the greenhouse at 21°–29° C. and watered by sprinkling. The seeds of the weed species were planted 10–12 days before treatment. In general, grasses were sprayed at a 3 to 4 leaf stage and broadleaves at a 1 to 2 leaf stage. Yellow nutsedge was 5 to 7 cm tall at application. Watering of the treated flats was confined to the soil surface and not to the foliage of the germinated plants. The degree of weed control was visually assessed and recorded 17–21 days after treatment, as percentage control compared to the growth of the same species in an untreated check flat of the same age.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that a test was not performed at that level of application.

Results listed in Table II below, expressed as average control of the three grasses (GR) (wild oat, barnyard grass, foxtail) and three broadleaf weeds (BL) (morningglory, mustard, velvetleaf), and yellow nutsedge (NS) are for an application rate of 4.0 kg/ha of the tested compound. Table III demonstrates the average control of the same weed species based on an application rate of 1.0 kg/ha for the tested compounds.

TABLE II

% CONTROL OF WEED SPECIES AT 4.00 kg/ha

| Compound | Preemergence | | | Postemergence | | |
|---|---|---|---|---|---|---|
| No. | GR avg. | BL avg. | NS | GR avg. | BL avg. | NS |
| 1 | 100 | 100 | 10 | 98 | 100 | 60 |
| 2 | 31 | 33 | 0 | 16 | 63 | 0 |
| 3 | 13 | 30 | 0 | 26 | 80 | 0 |
| 4 | 12* | 26 | 0 | 6 | 36 | 0 |
| 5 | 100* | 36 | 0 | 63 | 70 | 0 |
| 6 | 92* | 11 | 0 | 13 | 50 | 0 |
| 7 | 100* | 86 | 0 | 63 | 93 | 0 |
| 8 | 5* | 3 | 0 | 23 | 41 | 5 |
| 9 | 83 | 78 | 5 | 58 | 73 | 5 |
| 10 | 58 | 40 | 0 | 15 | 76 | 0 |
| 11 | 43 | 66 | 5 | 66 | 100 | 5 |
| 12 | 36 | 20 | 0 | 5 | 75 | 0 |
| 13 | 56 | 25 | 0 | 51 | 66 | 5 |
| 14 | 86 | 100 | 0 | 100 | 100 | 60 |
| 15 | 0 | 8 | 0 | 3 | 45 | 0 |
| 16 | 73 | 40 | 0 | 83 | 100 | 10 |
| 17 | 75 | 11 | 0 | 33 | 75 | 15 |
| 18 | 48 | 36 | 0 | 43 | 70 | 10 |
| 19 | 35 | 3 | 0 | 26 | 86 | 5 |
| 20 | 100 | 100 | 15 | 96 | 99 | 5 |
| 21 | 45 | 53 | 0 | 28 | 58 | 0 |
| 22 | 83 | 45 | 50 | 86 | 100 | 30 |
| 23 | 99 | 96 | 20 | 100 | 100 | 10 |
| 24 | 36 | 13 | 0 | 36 | 46 | 0 |
| 25 | 100 | 90 | 10 | 72 | 68 | 5 |
| 26 | 3 | 0 | 0 | 16 | 10 | 0 |
| 27 | 38 | 13 | 0 | 42 | 58 | 0 |
| 28 | 45 | 16 | 0 | 75 | 100 | 5 |
| 29 | 36 | 30 | 0 | 15 | 60 | 5 |
| 30 | 40 | 93 | 0 | 48 | 100 | 15 |
| 31 | 36 | 8 | 0 | 36 | 80 | 10 |
| 32 | 3 | 10 | 0 | 20 | 61 | 5 |
| 33 | 73 | 36 | 0 | 61 | 68 | 5 |
| 34 | 10 | 18 | 0 | 1 | 43 | 0 |
| 35 | 95 | 100 | 10 | 96 | 100 | 10 |
| 36 | 78 | 93 | 10 | 99 | 100 | 10 |
| 37 | 45 | 63 | 0 | 91 | 100 | 30 |
| 38 | 0 | 0 | 0 | 8 | 60 | 0 |
| 39 | 26 | 60 | 5 | 41 | 98 | 0 |
| 40 | 0 | 0 | 0 | 11 | 38 | 0 |
| 41 | 83 | 86 | 5 | 86 | 100 | 30 |
| 42 | 70 | 60 | 20 | 100 | 100 | 30 |
| 43 | 60 | 16 | 5 | 66 | 100 | 10 |
| 44 | 0 | 0 | 0 | 5 | 60 | 0 |
| 45 | 80 | 76 | 0 | 48 | 100 | 5 |
| 46 | 36 | 73 | 0 | 51 | 100 | 10 |
| 47 | 63 | 75 | 0 | 43 | 100 | 5 |
| 48 | 36 | 73 | 0 | 38 | 100 | 15 |
| 49 | 93 | 95 | 0 | 95 | 100 | 30 |
| 50 | 0 | 0 | 0 | 0 | 6 | 0 |
| 51 | 100 | 100 | 95 | 100 | 100 | 100 |
| 52 | 3 | 13 | 0 | 23 | 100 | 5 |
| 53 | 8 | 45 | 0 | 16 | 98 | 10 |
| 61 | 63 | 45 | 0 | 70 | 83 | 15 |
| 62 | 40 | 43 | 0 | 66 | 73 | 5 |

*Green foxtail not tested in this series.

TABLE III

% CONTROL OF WEED SPECIES AT 1.00 kg/ha

| Compound | Preemergence | | | Postemergence | | |
|---|---|---|---|---|---|---|
| No. | GR avg. | BL avg. | NS | GR avg. | BL avg. | NS |
| 54 | 81 | 96 | 10 | 100 | 100 | 50 |
| 55 | 56 | 36 | 0 | 43 | 71 | 15 |
| 56 | 50 | 11 | 0 | 71 | 100 | 10 |
| 57 | 38 | 16 | 0 | 18 | 68 | 10 |
| 58 | 71 | 15 | 0 | 71 | 68 | 10 |
| 59 | 42 | 38 | 0 | 38 | 68 | 10 |
| 63 | 38 | 31 | 0 | 98 | 100 | 20 |
| 64 | 53 | 36 | 0 | 95 | 100 | 10 |
| 65 | 50 | 20 | 0 | 86 | 100 | 10 |
| 66 | 33 | 6 | 0 | 70 | 100 | 5 |
| 67 | 66 | 15 | 0 | 80 | 86 | 20 |
| 68 | 15 | 8 | 0 | 63 | 100 | 10 |
| 69 | 13 | 36 | 0 | 38 | 100 | 10 |
| 70 | 20 | 36 | 0 | 21 | 100 | 10 |
| 71 | 30 | 3 | 0 | 76 | 73 | 10 |
| 72 | 96 | 76 | 60 | 86 | 100 | 40 |
| 79 | 70 | 70 | 5 | 25 | 90 | 10 |
| 80 | 98 | 100 | 5 | 91 | 100 | 50 |
| 81 | 55 | 68 | 5 | 65 | 100 | 20 |
| 82 | 60 | 100 | 10 | 94 | 100 | 10 |
| 83 | 43 | 15 | 5 | 60 | 100 | 5 |
| 84 | 95 | 100 | 60 | 100 | 100 | 85 |
| 85 | 38 | 70 | 5 | 46 | 100 | 20 |
| 86 | 47 | 83 | 15 | 21 | 100 | 15 |
| 87 | 53 | 46 | 5 | 36 | 96 | 20 |
| 88 | 43 | 83 | 5 | 91 | 100 | 30 |
| 89 | 0 | 0 | 0 | 51 | 100 | 30 |
| 90 | 45 | 76 | 0 | 43 | 93 | 25 |
| 91 | 60 | 96 | 5 | 50 | 100 | 20 |
| 92 | 85 | 100 | 100 | 100 | 100 | 85 |
| 93 | 78 | 96 | 30 | 98 | 100 | 15 |
| 94 | 46 | 100 | 20 | 100 | 100 | 40 |
| 95 | 100 | 100 | 100 | 100 | 100 | 100 |
| 96 | 98 | 100 | 50 | 98 | 100 | 70 |
| 97 | 100 | 100 | 100 | 100 | 100 | 100 |
| 107 | 100 | 100 | 98 | 100 | 100 | 90 |

In practice, a pure compound can be used as an herbicide. However, in general, the compounds are first formulated with one or more inert carriers or diluents suitable for herbicidal, use, before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; anitfoaming agents; and other substances as mentioned herein. Solid carriers or diluents included in such compositions or formulations may include, for example, ground natural minerals such as kaolins, alumina, calcium carbonate, silica, kiesel-guhr, clay, etc.; ground synthetic minerals such as various silicates and aluminosilicates and ground vegetable products such as bark, cornmeal, sawdust, cellulose powder and the like. To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrene-butadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.01 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | |
|---|---|
| Ingredient | Weight % |
| Oil | |
| Active Compound | 1 |
| Oil solvent-heavy aromatic naphtha | 99 |
| Total | 100 |
| Emulsifiable Concentrate | |
| Active Compound | 50 |
| Kerosene | 45 |
| Emulsifying agent (mixture of long chain ethoxylated polyethers with long chain sulfonate) | 5 |
| Total | 100 |
| Emulsifiable Concentrate | |
| Active Compound | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Active Compound | 0.5 | 50.0 | 90.0 |
| Attapulgite clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

33

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

[* These compounds are preferably employed in combination with a safener such as 2,2-dichloro-N,N-di-2-propenylacetamide (dichlormid).]

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and glufosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the

34 methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

Although the invention has been described with reference to preferred embodiments and examples thereof, it is not intended that the present invention be limited to only those described embodiments. The description of the preferred embodiments contained herein is intended in no way to limit the scope of the invention. As will be appreciated by a person skilled in the art, modifications and adaptations of the above-described invention can be made without departing from the spirit and scope of the invention, which is defined and circumscribed by the appended claims.

What is claimed is:

1. A substituted benzotriazole compound of having the formula

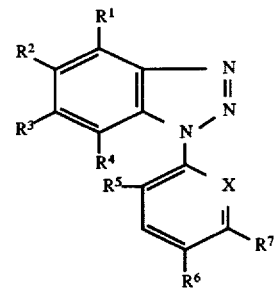

in which:

R$^1$, R$^2$ and R$^3$ may independently be hydrogen; halogen; nitro; hydroxy; cyano; alkyl; amino; alkoxyiminoalkyl; cyanoalkyl; carboxyalkyl; carboalkoxyalkyl; cyano (carboalkoxy)alkyl; hydroxyalkyl; alkoxyalkyl; alkylsulfonylaminoalkyl; haloalkylsulfonylaminoalkyl; (alkyl)$_n$aminoalkyl; (alkylcarbonyloxy)$_2$alkyl; haloalkyl; formyl; alkylcarbonyl; carboxy or its salts; COOalkyl; carboxamido; mono or di-substituted carboxamido wherein the nitrogen substituents are selected from alkyl, haloalkylsulfonyl, and alkylsulfonyl; sulfonamido wherein the nitrogen is optionally substituted with alkyl; (alkylsulfonyl)$_2$amino; (acetyl)$_2$amino;

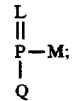

wherein Y is O, NR$^9$, or S(O)$_n$; and R$^8$ is (R$^{10}$)$_m$—COR$^{11}$; —(R$^{10}$)$_m$—SO$_2$R$^{11}$;

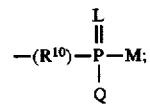

alkyl; haloalkyl; hydroxyalkyl; cyanoalkyl; acetoxyalkyl; alkoxyalkyl; hydroxy; alkenyl or alkynyl;

R$^9$ is hydrogen; alkyl; alkynyl; alkenyl or alkylcarbonyl;

R$^{10}$ is alkylene;

R$^{11}$ is alkyl; haloalkyl; hydrogen; hydroxy; alkoxy; haloalkoxy; alkoxyalkyl; alkoxyalkoxy; alkoxyalkylamino; dialkoxyalkylamino; alkoxycarbonyl; hydroxycarbonyl; alkoxycarbonylalkyl; hydroxycarbonylalkyl; (alkyl)$_n$amino; (alkyl)$_n$hydrazino; alkoxycarbonylalkylamino; hydroxyalkylamino; (alkyl)$_n$aminoalkylamino; (alkyl)$_n$animocarbonylalkylamino; hydroxycarbonylalkylamino; alkylsulfonylamino; acetylarninoalkylamino; N-alkoxy-N-(alkyl)$_m$amino; N-hydroxy-N-(alkyl)$_m$amino; cyanoalkylamino; (alkenyl)$_n$amino; alkoxyalkylamino; (alkynyl)$_n$amino; alkenyloxy; alkynyloxy or semicarbazido;

m is 0 or 1;

n is 0, 1 or 2;

z is 1 or 2;

q is 0 or 1;

M and Q are independently alkoxy; alkyl; (alkyl)$_n$amino; hydroxy; hydrogen; alkenyloxy; (alkenyl)$_n$amino; alkynyloxy; or (alkynyl)$_n$amino;

L is oxygen or sulfur;

P is phosphorous;

$R^4$ is hydrogen, halogen, alkyl or nitro;

$R^5$ is halogen; cyano; alkylthio; alkylsulfinyl; alkylsulfonyl; alkoxy; acetylamino or amino;

$R^6$ is haloalkyl; haloalkoxy; or SO$_y$R$^{12}$ and $R^{12}$ is alkyl or haloalkyl and y is 0, 1 or 2;

$R^7$ is hydrogen or halogen;

X is CR$^{13}$ wherein $R^{13}$ is hydrogen; halogen; haloalkyl; cyano; alkylthio; alkylsulfonyl; alkylsufinyl or alkoxy; with the proviso that when X is CR$^{13}$ and $R^1$, $R^3$, $R^4$, $R^7$ and $R^{13}$ are hydrogen, at least one of $R^2$, $R^5$ and $R^6$ is not chloro; and when X is CR$^{13}$, $R^5$ is acetylamino, halogen or amino and $R^1$, $R^2$, $R^3$, $R^4$, $R^7$, $R^{13}$ are hydrogen, then $R^6$ is not SO$_2$CH$_2$Cl; or an agriculturally acceptable salt thereof.

2. A compound according to claim 1 wherein $R^1$ is hydrogen, halogen, cyano, alkyl or haloalkyl; $R^2$ is hydrogen, nitro, haloalkyl, halogen, or alkyl; $R^3$ is hydrogen, halogen or YR$^8$; $R^4$ is hydrogen; $R^5$ is halogen; $R^6$ is haloalkyl or SO$_y$R$^{13}$; $R^7$ is hydrogen and X is C-halogen, C-hydrogen or C-haloalkyl.

3. A compound according to claim 2 wherein $R^1$ is hydrogen, cyano or halogen; R2 is hydrogen, haloalkyl or halogen; $R^6$ is haloalkyl and X is C-halogen.

4. A compound according to claim 2 wherein $R^1$ is hydrogen; $R^2$ is hydrogen, halogen or alkyl; $R^3$ is OR$^8$ wherein $R^8$ is alkyl, alkenyl, alkynyl, cyanoalkyl and haloalkyl; $R^4$ is hydrogen; $R^5$ is halogen; $R^6$ is haloalkyl; $R^7$ is hydrogen and X is C-halogen or C-hydrogen.

5. A compound according to claim 1 wherein $R^1$is hydrogen, halogen, alkyl or cyano; $R^2$ is hydrogen, haloalkyl, alkyl or halogen and $R^3$ is YR$^8$.

6. A compound according to claim 5 wherein $R^3$ is YR$^8$ and Y is O; $R^4$ is hydrogen; $R^5$ is hydrogen or halogen; $R^6$ is haloalkyl; $R^7$is hydrogen and X is C-halogen.

7. A compound according to claim 5 wherein $R^3$ is YR$^8$ and Y is NR$^9$; $R^4$ is hydrogen; $R^5$ is hydrogen or halogen; $R^6$ is haloalkyl; $R^7$ is hydrogen and X is C-halogen.

8. A compound according to claim 5 wherein $R^3$ is YR$^8$ and Y is S(O)$_n$; $R^4$ is hydrogen; $R^5$ is hydrogen or halogen; $R^6$ is haloalkyl; $R^7$ is hydrogen and X is C-halogen.

9. A compound according to claim 2 wherein $R^1$ is hydrogen; $R^2$ is chloro, fluoro, or trifluoroalkyl; $R^3$ is hydrogen; $R^4$ is hydrogen; $R^5$ is hydrogen or halogen; $R^6$ is haloalkyl; $R^7$is hydrogen and X is C-halogen.

10. A compound according to claim 1 wherein $R^1$ is hydrogen; $R^2$ is nitro; $R^3$ is hydrogen; $R^4$ is hydrogen; $R^5$ is chloro; $R^6$ is CF$_3$; $R^7$ is hydrogen and X is C—Cl.

11. A herbicidal composition comprising
a) a herbicidally effective amount of a compound according to claim 1, and;
b) a diluent or carrier suitable for use with herbicides.

12. A herbicidal composition according to claim 11 wherein $R^1$ is hydrogen, cyano, alkyl, haloalkyl or halogen; $R^2$ is hydrogen, alkyl, nitro, haloalkyl or halogen; $R^3$ is hydrogen, halogen or YR$^8$; $R^4$ is hydrogen; $R^5$ is hydrogen or halogen; $R^6$ is haloalkyl; $R^7$ is hydrogen and X is CR$^{13}$ wherein $R^{13}$ is hydrogen, halogen or haloalkyl.

13. A composition according to claim 12 wherein $R^1$ is hydrogen; $R^2$ is hydrogen, alkyl or halogen; $R^6$ is CF$_3$ and X is C-chloro.

14. A method of controlling undesirable vegetation in the presence of a crop comprising applying to such vegetation or a locus thereof a herbicidally effective amount of a compound according to claim 1.

15. A method according to claim 14 wherein the crop is corn.

* * * * *